(12) United States Patent
Teshigahara et al.

(10) Patent No.: US 7,217,680 B2
(45) Date of Patent: May 15, 2007

(54) METHOD FOR PRODUCING COMPOSITE OXIDE CATALYST

(75) Inventors: Isao Teshigahara, Mie (JP); Hisao Kinoshita, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 192 days.

(21) Appl. No.: 11/032,072

(22) Filed: Jan. 11, 2005

(65) Prior Publication Data

US 2005/0261521 A1   Nov. 24, 2005

Related U.S. Application Data

(63) Continuation of application No. PCT/JP2004/13462, filed on Sep. 15, 2004.

(30) Foreign Application Priority Data

May 21, 2004   (JP) ............................. 2004-151997

(51) Int. Cl.
*B01J 23/00*   (2006.01)
*C07C 51/235*   (2006.01)

(52) U.S. Cl. ...................... 502/312; 562/535

(58) Field of Classification Search ............... None
See application file for complete search history.

(56) References Cited

U.S. PATENT DOCUMENTS 5,959,143 A * 9/1999 Sugi et al. .................. 562/534

FOREIGN PATENT DOCUMENTS

| JP | 61-114739 | 6/1986 |
|----|-----------|--------|
| JP | 4-79697 | 12/1992 |
| JP | 7-89726 | 4/1995 |
| JP | 8-206504 | 8/1996 |
| JP | 2001-79408 | 3/2001 |
| JP | 2003-210991 * | 7/2003 |
| JP | 2003-251184 | 9/2003 |

OTHER PUBLICATIONS

U.S. Appl. No. 11/032,050, filed Jan. 11, 2005, Teshigahara, et al.
U.S. Appl. No. 11/033,131, filed Jan. 12, 2005, Teshigahara, et al.
U.S. Appl. No. 11/033,271, filed Jan. 12, 2005, Teshigahara, et al.
U.S. Appl. No. 11/044,187, filed Jan. 28, 2005, Teshigahara, et al.
U.S. Appl. No. 11/045,123, filed Jan. 31, 2005, Tazawa, et al.
U.S. Appl. No. 11/045,307, filed Jan. 31, 2005, Tazawa, et al.
Patent Abstracts of Japan, JP 61-114739, Jun. 2, 1986.

* cited by examiner

*Primary Examiner*—Paul A. Zucker
(74) *Attorney, Agent, or Firm*—Oblon, Spivak, McClelland, Maier & Neustadt, P.C.

(57) ABSTRACT

A method for producing a composite oxide catalyst for gas phase catalytic oxidation of an unsaturated aldehyde with a molecular oxygen-containing gas to produce the corresponding unsaturated carboxylic acid in good yield, is presented. A method for producing a composite oxide catalyst, which is a method for producing a composite oxide catalyst having the following formula (I), characterized in that $Sb_2O_3$ of isometric system is used as at least a part of an antimony-supplying source compound:

$$Mo_{12}X_aV_bSb_cCu_dSi_eC_fO_g \qquad (I)$$

(wherein the respective components and variables have the following meanings:
X is at least one element selected from the group consisting of Nb and W; a, b, c, d, e, f and g represent atomic ratios of the respective elements, and against 12 of molybdenum atom, $0<a\leq10$, $0<b\leq10$, $0<c\leq5$, $0<d\leq5$, $0\leq e\leq1,000$, and $0\leq f\leq1,000$, and g is a number determined by the degrees of oxidation of the above respective components.)

7 Claims, No Drawings

METHOD FOR PRODUCING COMPOSITE OXIDE CATALYST

TECHNICAL FIELD

The present invention relates to a method for producing a composite oxide catalyst for gas phase catalytic oxidation of an unsaturated aldehyde with a molecular oxygen-containing gas to produce the corresponding unsaturated carboxylic acid in good yield.

BACKGROUND ART

Heretofore, various proposals have been made with respect to catalysts for gas phase catalytic oxidation of an unsaturated aldehyde such as acrolein or methacrolein with molecular oxygen to produce an unsaturated carboxylic acid such as acrylic acid or methacrylic acid. These catalysts are required to have a high conversion of the unsaturated aldehyde or a high selectivity for the unsaturated carboxylic acid as the desired product, as far as possible, from the viewpoint of the effective utilization of the unsaturated aldehyde material to be produced from an olefin and streamlining of the process steps in the reaction. In such a case, for example, the reaction to produce acrylic acid from acrolein is carried out usually in a scale of 3,000,000 tons/year, and if the above conversion or selectivity is improved by 0.1%, the amount of acrylic acid as the product to be obtained, will be remarkably increased at a level of a few hundreds to a few thousands tons. Accordingly, improvement of the catalyst performance such as the conversion or selectivity, even if it is a little improvement, will substantially contribute to the effective utilization of the resource or streamlining of the process steps.

Heretofore, various proposals have been made with an aim to improve the catalytic performance such as the starting material conversion or selectivity in the reaction, and various proposals have been made also with respect to an antimony-supplying source compound.

For example, Patent Document 1 discloses a method for producing a Mo—V type oxide catalyst represented by $MoV_aW_bCu_cX_dY_eZ_fO_h$ (wherein X is at least one element selected from Sb and Sn, Y is at least one element selected from Mg, Ca, Sr and Ba, Z is at least one element selected from Ti, Zr and Ce, and O represents oxygen, a, b, c, d, e, f, g and h represent atomic ratios of the respective elements, when a=12, $2 \leq b \leq 14$, $0 \leq c \leq 12$, $0 < d \leq 6$, $0 < e \leq 5$, $0 \leq f \leq 3$ and $0 \leq g \leq 10$, and h takes a numerical value determined by the oxidized states of the respective elements), wherein at least one type of antimony oxides wherein the valency of antimony is larger than 0 and less than 5, is used as at least a part of the antimony-supplying source.

Further, Patent Document 2 discloses a method for preparing a catalyst for the production of an unsaturated carboxylic acid, which contains at least phosphorus, molybdenum and antimony in the catalyst composition, characterized in that antimony trioxide having an average particle diameter of at most 0.2 μm, is used as the starting material.

Further, Patent Document 3 discloses a catalyst which has a composition represented by $Mo_{12}V_aW_bCu_cSb_dX_eY_fZ_gO_h$ (wherein X is at least one element selected from the group consisting of an alkali metal and thalium, Y is at least one element selected from the group consisting of Mg, Ca, Sr, Ba and Zn, Z is at least one element selected from the group consisting of Nb, Ce, Sn, Cr, Mn, Fe, Co, Sm, Ge, Ti and As, a, b, c, d, e, f, g and h represent atomic ratios of the respective elements, against 12 of Mo atom, $0 < a \leq 10$, $0 \leq b \leq 10$, $0 < c \leq 6$, $0 < d \leq 10$, $0 \leq e \leq 0.5$, $0 \leq f \leq 1$ and $0 \leq g < 6$, and h is the number of oxygen atoms required to satisfy the valencies of the above respective components) and which is prepared by using antimony acetate as an antimony material source at the time of preparation of the catalyst active component.

These conventional composite oxide catalysts exhibit excellent properties respectively, but a still higher conversion of the starting material unsaturated aldehyde or still higher selectivity for an unsaturated carboxylic acid, is desired.

Patent Document 1: JP-A-8-206504
Patent Document 2: JP-B-4-79697
Patent Document 3: JP-A-2001-79408

DISCLOSURE OF THE INVENTION

PROBLEM TO BE SOLVED BY THE INVENTION

The present invention is to provide a method for producing a composite oxide catalyst which presents a high conversion of a starting material unsaturated aldehyde and a high selectivity for an unsaturated carbocyclic acid at the time of gas phase catalytic oxidation of the unsaturated aldehyde with a molecular oxygen-containing gas to produce the unsaturated carboxylic acid.

MEANS TO SOLVE THE PROBLEM

The present inventors have conducted an extensive research to accomplish the above object and have found that in a method for producing a composite oxide catalyst for the production of an unsaturated carboxylic acid, which contains at least Mo and V as components, the catalyst performance can be improved by using $Sb_2O_3$ of isometric system as at least a part of the antimony-supplying source compound.

The means of employing $Sb_2O_3$ having the specific crystal phase as the antimony starting material in the present invention, is not disclosed in the above-mentioned Patent Documents 1 to 3. $Sb_2O_3$ may have an isometric system (which has the main peak at $2\theta=27.6°$ in the X-ray diffraction (anticathode Cu—Kα)) or a rhombic system (which has the main peak at $2\theta=28.3°$ in the X-ray diffraction (anticathode Cu—Kα)). According to the finding by the present inventors, it has been found that the excellent characteristic is obtainable when $Sb_2O_3$ having the isometric system is used as the antimony-supplying source compound of the catalyst. The reason is not clearly understood, but it is considered that as compared with one of rhombic system, $Sb_2O_3$ of isometric system is readily taken into the Mo—V structure in the catalyst of the present invention.

Thus, the present invention is characterized by the following constructions.

(1) A method for producing a composite oxide catalyst, which is a method for producing a composite oxide catalyst having the following formula (I), to be used at the time of gas phase catalytic oxidation of an unsaturated aldehyde with a molecular oxygen-containing gas to produce the corresponding unsaturated carboxylic acid, characterized in that $Sb_2O_3$ of isometric system is used as at least a part of an antimony-supplying source compound:

$$Mo_{12}X_aV_bSb_cCu_dSi_eC_fO_g \qquad (I)$$

(wherein the respective components and variables have the following meanings:

X is at least one element selected from the group consisting of Nb and W; a, b, c, d, e, f and g represent atomic ratios of the respective elements, and against 12 of molybdenum atom, $0<a\leq 10$, $0<b\leq 10$, $0<c\leq 5$, $0<d\leq 5$, $0\leq e\leq 1,000$ and $0\leq f\leq 1,000$, and g is a number determined by the degrees of oxidation of the above respective components.)

(2) The method for producing a composite oxide catalyst according to the above (1), wherein $Sb_2O_3$ is used as the antimony-supplying source compound, and the ratio ($a_1/a_2$) of the intensity ($a_1$) at $2\theta$=about 28.3 to the intensity ($a_2$) at $2\theta$=about 27.6, of its X-ray diffraction (anticathode Cu—K$\alpha$), is at most 0.2.

(3) The method for producing a composite oxide catalyst according to the above (1) or (2), wherein the Si and C components-supplying source compound is silicon carbide.

(4) The method for producing a composite oxide catalyst according to any one of the above (1) to (3), wherein an aqueous solution or aqueous dispersion of supply source compounds containing the respective catalyst component elements shown by the formula (I), is prepared, and such an aqueous solution or aqueous dispersion is dried to a powder, which is molded by using at least one binder selected from the group consisting of silica, graphite and cellulose, and the molded product is calcined.

(5) A composite oxide catalyst produced by the method as defined in any one of the above (1) to (4).

(6) A method which comprises gas phase catalytic oxidation of acrolein with a molecular oxygen-containing gas in the presence of the composite oxide catalyst as defined in the above (5), to produce the corresponding acrylic acid.

EFFECTS OF THE INVENTION

The present invention provides a method for producing a composite oxide catalyst which presents a high conversion of a starting material unsaturated aldehyde and a high selectivity for an unsaturated carboxylic acid in the production of the unsaturated carboxylic acid by gas phase catalytic oxidation of the unsaturated aldehyde with a molecular oxygen-containing gas.

BEST MODE FOR CARRYING OUT THE INVENTION

The composite oxide catalyst according to the present invention is a composite oxide catalyst having the following formula (I), characterized in that $Sb_2O_3$ of isometric system is used as at least a part of an antimony-supplying source compound.

$$Mo_{12}X_aV_bSb_cCu_dSi_eC_fO_g \qquad (I)$$

(wherein the respective components and variables have the following meanings:

X is at least one element selected from the group consisting of Nb and W; a, b, c, d, e, f and g represent atomic ratios of the respective elements, and against 12 of molybdenum atom, $0<a\leq 10$, $0<b\leq 10$, $0<c\leq 5$, $0<d\leq 5$, $0\leq e\leq 1,000$ and $0\leq f\leq 1,000$, and g is a number determined by the degrees of oxidation of the above respective components.)

The composite oxide catalyst of the present invention can be obtained by integrating supply source compounds of the respective catalyst components shown by the formula (I), in an aqueous system, followed by heating.

Here, "integrating" means that in an aqueous system preferably made of an aqueous solution or aqueous dispersion, supply source compounds containing the respective catalyst component elements are mixed and, if necessary, subjected to aging treatment, so that the respective elements are integrally contained.

Namely, each of (A) a method wherein the above respective supply source compounds are mixed all at once, (B) a method wherein the above respective supply source compounds are mixed all at once and further subjected to aging treatment, (C) a method wherein the above respective supply source compounds are stepwisely mixed, (D) a method wherein stepwise mixing of the above respective supply source compounds, followed by aging treatment, is repeated, and a method comprising a combination of (A) to (D), is included in the concept of integrating supply source compounds of the respective catalyst component elements in an aqueous system.

Here, "aging" means "an operation wherein an industrial material or semi-product is treated under specific conditions such as prescribed time, prescribed temperature, etc., to obtain or improve the required physical properties or chemical properties, to facilitate the prescribed reaction, etc." as disclosed also in Encyclopedia Chimica (published by Kyoritsu Shuppan CO., LTD., in 1963). Here, the above prescribed time is preferably within a range of from one minute to 24 hours in the present invention, and the above prescribed temperature is preferably within a range of from room temperature to 200° C.

In the above integration, not only the supply source compounds of the respective elements, but also a carrier material such as alumina, silica or a refractory oxide may be included as a component for such integration.

Further, the above heating is meant for heat treatment to form the respective oxides or composite oxides of the above supply source compounds of the respective catalyst component elements, to form an oxide or composite oxide of a composite compound formed by the integration or to form the final composite oxide. And, the heating is not limited to only once. Namely, such heating may optionally be carried out at each step for integration shown by the above (A) to (D), and such heating may be additionally carried out after the integration, as the case requires. The temperature for such heating is usually preferably within a range of from 160° C. to 600° C.

Further, in the above integration and heating, in addition to such operations, drying, pulverization or molding, may, for example, be carried out before, after or during such operations.

Further, the supply source compounds of the respective catalyst component elements of the present invention are meant for compounds which contain one or more elements among component elements constituting the composite oxide catalyst and which are capable of being formed into an aqueous solution or aqueous suspension, i.e. compounds of catalyst-constituting elements to be used as raw materials for the production. Accordingly, the supply source compounds may be compounds which may be converted to oxides by calcining.

In the present invention, $Sb_2O_3$ is used as at least a part of the supply source compound of antimony. As mentioned above, $Sb_2O_3$ may have an isometric system (which has the main peak at $2\theta=27.6°$ in the X-ray diffraction (anticathode Cu—K$\alpha$)) or a rhombic system (which has the main peak at $2\theta=28.3°$ in the X-ray diffraction (anticathode Cu—Kα)). In the present invention, one having an isometric system is used.

In the present invention, it is not necessary that $Sb_2O_3$ of isometric system is used for the entirety of the antimony-supplying source compound, and it is used preferably at lest 80 wt %, particularly preferably at least 90 wt %, of the antimony-supplying source compound. For example, in a case where a mixture with $Sb_2O_3$ of rhombic system, is used, a mixture wherein the ratio $a_1/a_2$ of the intensity $(a_1)$ at $2\theta$=about 28.3° to the intensity $(a_2)$ at $2\theta$=about 27.6°, is preferably at most 0.2, particularly preferably at most 0.1, is used, whereby a catalyst having an adequate catalyst performance can be obtained.

With respect to the supply source compounds of the respective catalyst components other than antimony, halides, sulfates, nitrates, ammonium salts, oxides, carboxylates, ammonium carboxylates, ammonium halides, hydroacids, acetylacetonates or alkoxides of the respective elements, may, for example, be mentioned.

The following may be mentioned as preferred specific examples of the supply source compounds of the respective catalyst components. A Mo-supplying source compound may be a molybdenum compound such as ammonium paramolybdate, molybdenum tetraoxide, molybdic acid, ammonium phosphorus molybdate or phosphorus molybdic acid; a Cu-supplying source compound may be a copper compound such as cuprous chloride or copper sulfate; a W-supplying source compound may be a tungsten compound such as ammonium paratungstate or tungstic acid; a Nb-supplying source compound may be a niobium compound such as niobium hydroxide, niobium oxalate or ammonium niobium oxalate; and a V-supplying source compound may be a vanadium compound such as ammonium methavanadate or vanadium oxide.

As a Si and C components-supplying source compound, silicon carbide containing a chemical bond of Si and C may be mentioned as a preferred example, for a reason that it is inactive and has good thermal conductivity.

Now, specific examples of the process steps for the production of the composite oxide catalyst of the present invention will sequentially be described. Firstly, an aqueous solution or aqueous dispersion of the supply source compounds of the respective catalyst component elements will be prepared. Hereinafter, such an aqueous solution or aqueous dispersion will be referred to as a slurry solution unless otherwise specified.

Such a slurry solution can be obtained by uniformly mixing the supply source compounds of the respective catalyst component elements and water uniformly. In the present invention, the slurry solution is preferably an aqueous solution. The ratio of the compounds of the respective constituting components in the slurry solution is adjusted so that the atomic ratio of the respective catalyst component elements will be within the range of the above formula (I).

The amount of the above-mentioned water to be used is not particularly limited so long as it is an amount whereby the entire amounts of the supply source compounds can be completely dissolved or uniformly mixed, and it may be suitably determined taking into the following heat treating method, temperature, etc. into consideration. The amount of water to be used, is usually from 100 to 2,000 parts by weight per 100 parts by weight of the total amount of the supply source compounds. If the amount of water is less than the above prescribed amount, the compounds may sometimes not completely be dissolved or not uniformly be mixed. Further, if the amount of water exceeds the above prescribed amount, there will be a problem that the energy costs for the heat treatment will be increased. In many cases, the aqueous dispersion in a slurry form is preferably subjected to aging treatment preferably from room temperature to 200° C. for from one minute to 24 hours.

Then, the slurry solution obtained in the above step is dried to obtain a powder. The drying method is not particularly limited so long as it is thereby possible to dry the slurry solution completely and obtain a powder. For example, drum drying, freeze drying or spray drying may be mentioned as a preferred method.

Spray drying is a method which is preferably applied in the present invention, since it is thereby possible to dry the solution from the slurry solution state to a uniform powder state in a short time. The temperature for drying may vary depending upon the concentration of the slurry solution or upon the transportation speed of the solution, but the temperature at the outlet of the dryer is preferably from 90 to 180° C. Further, it is preferred to carry out the drying so that the particle diameter of the dried powder will be from 10 to 200 µm. The powder may be pulverized after drying, as the case requires. Thus, a precursor containing the catalyst-constituting components, will be obtained.

The composite oxide catalyst obtainable by the method of the present invention, may also be obtained by molding the above-mentioned powder. The molding method is not particularly limited, and it is preferred to mix the powder with a molding assistant such as a binder, followed by molding. A preferred assistant may, for example, be silica, graphite or crystalline cellulose when the powder is subjected to tabletting, and it may be a silica gel, diatomaceous earth or alumina powder when the powder is subjected to extrusion molding. The molding assistant is used preferably in an amount of from about 0.5 to 10 parts by weight per 100 parts by weight of the powder.

Further, it is possible to improve the mechanical strength of the catalyst by using, as a reinforcing material, inorganic fibers such as ceramic fibers or whiskers, as the case requires. However, fibers which are reactive with the catalyst component, such as potassium titanate whiskers or basic magnesium carbonate whiskers, are not desirable. As the reinforcing material, ceramic fibers are particularly preferred. The amount of such fibers is usually from 1 to 30 parts by weight per 100 parts by weight of the heat-treated powder. The above molding assistant and reinforcing material are usually used as mixed with the heat-treated powder.

The powder mixed with the molding assistant, reinforcing material, etc., may be molded by a suitable molding method such as (A) tabletting, (B) extrusion molding or (C) support molding as a cover on a carrier of e.g. a spherical shape. With respect to the shape of the molded product, a suitable shape may be selected for use such as a pellet, spherical, columnar or ring shape. Among them, in the case of tabletting, a pellet or ring shape is preferred, and in the case of extrusion molding, a columnar or ring shape is preferred.

Then, the molded product is calcined to obtain a composite oxide catalyst. The calcining temperature is usually from 250 to 600° C., preferably from 300 to 420° C. The calcining time is from 1 to 50 hours. The calcining may be carried out in an atmosphere in the presence of an inert gas or molecular oxygen. However, it is preferably carried out in the presence of molecular oxygen. If the calcining temperature is too low, formation of active species tends to be inadequate, and if it is too high, decomposition of active species is likely to occur. The molecular oxygen in the atmospheric gas is preferably at most 10 vol %. If the content of the molecular oxygen exceeds 10 vol %, the activities of the catalyst may tend to be inadequate. The content of the molecular oxygen may be 0%, but is preferably at least 0.05 vol %.

The method of gas phase oxidation of an unsaturated aldehyde with molecular oxygen or a molecular oxygen-containing gas by using the catalyst produced by the present invention, to produce the corresponding unsaturated carboxylic acid, may be carried out by a conventional method. For example, as the reactor, a fixed bed tubular reactor may be employed. In such a case, the reaction may be a single flow process through the reactor, or may be a recycle process, and it may be carried out under such conditions as commonly employed in a reaction of this type.

For example, a mixed gas comprising from 1 to 15 vol % of acrolein, from 0.5 to 25 vol % of molecular oxygen, from 0 to 40 vol % of steam, from 20 to 80 vol % of an inert gas such as nitrogen, carbon dioxide gas or the like, etc., is introduced to a catalyst layer packed in each reaction zone of each reaction tube having an inner diameter of preferably from 15 to 50 mm at from 200 to 350° C. under a pressure of from 0.1 to 1 MPa at a space velocity (SV) of from 300 to 5,000 hr$^{-1}$. In the present invention, in order to further increase the productivity, the operation may be made under a higher load reaction condition, such as a higher raw material gas concentration or a higher space velocity. Thus, with the catalyst produced by the present invention, it is possible to produce acrylic acid in good yield and with high selectivity.

EXAMPLES

Now, the present invention will be described in further detail with reference to Examples and Comparative Examples. However, it should be understood that the present invention is by no means restricted to such Examples. Further, the conversion of acrolein, the selectivity for acrylic acid and the yield of acrylic acid are defined by the following formulae.

Conversion of acrolein (mol %): 100×(mols of reacted acrolein)/(mols of supplied acrolein)

Selectivity for acrylic acid (mol %): 100×(mols of formed acrylic acid)/(mols of reacted acrolein)

Yield of acrylic acid (mol %): 100×(mols of formed acrylic acid)/(mols of supplied acrolein)

Example 1

1,124 ml of pure water was heated, and 298.7 g of ammonium paramolybdate and 57.94 g of ammonium methavanadate were dissolved with stirring. To this aqueous solution, an aqueous solution having 32.45 g of ammonium niobium oxalate dissolved in 324 ml of pure water at 80° C., was added, and further, an aqueous solution having 70.24 g of copper sulfate dissolved in 95 ml of heated pure water, was added. To this aqueous solution, 20.54 g of isometric system antimony trioxide (ratio $a_1/a_2$ of the intensity ($a_1$) at 2θ=about 28.3° to the intensity ($a_2$) at 2θ=about 27.6°, in the X-ray diffraction (anticathode Cu—Kα)=0.05) was added and stirred. To this liquid, 848 g of a silicon carbide powder having a particle size distribution such that the maximum particle diameter was at most 63 μm, the particle diameter at a point of cumulative height of 3% was at most 50 μm, the particle diameter at a point of cumulative height of 50% was 25±2.0 μm, and the particle diameter at a point of cumulative height of 94% was at most 16 μm, was added and thoroughly stirred and mixed to obtain a slurry-form dispersion.

The slurry-form dispersion thus obtained was heated and dried at 130° C. The obtained powder was molded by a small size tabletting machine into a columnar shape having a height of 4 mm and a diameter of 5 mm, and the molded product was calcined in a calcining furnace in a nitrogen stream at 380° C. for 3 hours to obtain a catalyst.

The composition (excluding oxygen) of the obtained composite oxide catalyst is as follows.

$MO_{12}Nb_2V_{3.5}Cu_2Sb_1Si_{150}C_{150}$

To evaluate the obtained catalyst, 0.3 g of one pulverized and adjusted to from 20 to 28 mesh, was packed into a U-shape reaction tube having an inner diameter of 4 mm, and this reactor was put into a heated niter bath (temperature: 280° C.), and a gas having a composition comprising 4.3 vol % of acrolein, 8.8 vol % of oxygen, 41.5 vol % of steam and 45.3 vol % of nitrogen gas, was introduced and reacted at a SV (space velocity: the flow rate of the raw material gas per unit time/the apparent volume of the packed catalyst) of 18,000/hr.

Here, the above niter bath is a salt bath to carry out the reaction by inserting the reaction tube in a heating medium made of an alkali metal nitrate. This heating medium melts at a temperature of at least 200° C., is useful up to 400° C. and has a good heat removal efficiency, and thus, it is a reaction bath suitable for an oxidation reaction with a large quantity of heat generation.

As a result of the reaction, the conversion of acrolein was 99.7%, the selectivity for acrylic acid was 98.7%, and the yield of acrylic acid was 98.4%.

Example 2

A catalyst having the same composition as in Example 1 was produced under the same conditions as in Example 1 except that as the raw material of antimony, antimony trioxide (ratio $a_1/a_2$ of the intensity ($a_1$) at 2θ=about 28.3° to the intensity ($a_2$) at 2θ=about 27.6°, in the X-ray diffraction (anticathode Cu—Kα)=0.37), was used, and evaluation of the reactivity was carried out under the same reaction conditions.

As a result of the reaction, the conversion of acrolein was 99.2%, the selectivity for acrylic acid was 98.4%, and the yield of acrylic acid was 97.6%.

As described in the foregoing, in the Examples wherein isometric antimony trioxide was used as the antimony-supplying source compound, the conversion of acrolein, the selectivity for acrylic acid and the yield of acrylic acid, were all excellent, and the gas phase catalytic oxidation reaction of acrolein was carried out efficiently.

Especially when $Sb_2O_3$ was used as the antimony-supplying source compound, and the ratio ($a_1/a_2$) of the intensity ($a_1$) at 2θ=about 28.3° to the intensity ($a_2$) at 2θ=about 27.6°, in the X-ray diffraction (anticathode Cu—Kα) was at most 0.2, a still better result was obtained.

INDUSTRIAL APPLICABILITY

The composite oxide catalyst produced by the method of the present invention is useful for gas phase catalytic oxidation of an unsaturated aldehyde with a molecular oxygen-containing gas to produce the corresponding unsaturated carboxylic acid in good yield. The produced unsaturated carboxylic acid such as acrylic acid, is useful for a wide range of applications as e.g. a starting material for various chemical products, a monomer for common resins, a monomer for functional resins such as water absorptive resins, a flocculating agent or a thickener.

The entire disclosure of Japanese Patent Application No. 2004-151997 filed on May 21, 2004 including specification, claims and summary is incorporated herein by reference in its entirety.

What is claimed is:

1. A method for producing a composite oxide catalyst, which is a method for producing a composite oxide catalyst having the following formula (I), to be used at the time of gas phase catalytic oxidation of an unsaturated aldehyde with a molecular oxygen-containing gas to produce the corresponding unsaturated carboxylic acid, characterized in that $Sb_2O_3$ of isometric system is used as at least a part of an antimony-supplying source compound:

$$Mo_{12}X_aV_bSb_cCu_dSi_eC_fO_g \qquad (I)$$

where the respective components and variables have the following meanings:

X is at least one element selected from the group consisting of Nb and W;

a, b, c, d, e, f and g represent atomic ratios of the respective elements;

against 12 of molybdenum atom $0<a\leq10$, $0<b\leq10$, $0<c\leq5$, $0<d\leq5$, $0\leq e\leq1,000$ and $0\leq f\leq1,000$; and g is a number determined by the degrees of oxidation of the above respective components, wherein $Sb_2O_3$ is used as the antimony-supplying source compound; and the ratio $(a_1/a_2)$ of the intensity $(a_1)$ at $2\theta=$about $28.3°$ to the intensity $(a_2)$ at $2\theta=$about $27.6°$ of an X-ray diffraction (anticathode Cu—Kα) of the antimony-supplying source compound is at most 0.2.

2. The method for producing a composite oxide catalyst according to claim 1, wherein the Si and C components-supplying source compound is silicon carbide.

3. The method for producing a composite oxide catalyst according to claim 1, wherein an aqueous solution or aqueous dispersion of supply source compounds containing the respective catalyst component elements shown by the formula (I), is prepared, and such an aqueous solution or aqueous dispersion is dried to a powder, which is molded by using at least one binder selected from the group consisting of silica, graphite and cellulose, and the molded product is calcined.

4. A composite oxide catalyst produced by the method as defined in claim 1.

5. A method which comprises gas phase catalytic oxidation of acrolein with a molecular oxygen-containing gas in the presence of the composite oxide catalyst as defined in claim 4, to produce the corresponding acrylic acid.

6. The method for producing a composite oxide catalyst according to claim 1, wherein the antimony-supplying source compound comprises at least 80 wt % of the $Sb_2O_3$ of isometric system.

7. The method for producing a composite oxide catalyst according to claim 1, wherein the antimony-supplying source compound comprises at least 90 wt % of the $Sb_2O_3$ of isometric system.

* * * * *